United States Patent [19]
Minet et al.

[11] Patent Number: 5,202,517
[45] Date of Patent: Apr. 13, 1993

[54] PROCESS FOR PRODUCTION OF ETHYLENE FROM ETHANE

[75] Inventors: Ronald G. Minet, South Pasadena; Theodore T. Tsotsis, Huntington Beach; Althea M. Champagnie, Los Angeles, all of Calif.

[73] Assignee: Medalert Incorporated, South Pasadena, Calif.

[21] Appl. No.: 427,517

[22] Filed: Oct. 27, 1989

[51] Int. Cl.$^5$ ............................................. C07C 5/333
[52] U.S. Cl. ................................. 585/655; 585/633; 585/636; 585/660; 585/920; 585/921; 585/954
[58] Field of Search ............ 585/633, 636, 655, 660, 585/920, 921, 954

[56] References Cited

U.S. PATENT DOCUMENTS

| | | | |
|---|---|---|---|
| 3,290,406 | 12/1956 | Pfefferle | 585/954 |
| 4,271,730 | 2/1981 | Eastman. | |
| 4,327,238 | 4/1982 | Eastman. | |
| 4,791,079 | 12/1988 | Hazbun. | |

FOREIGN PATENT DOCUMENTS

| | | | |
|---|---|---|---|
| 614611 | 2/1961 | Canada | 585/954 |
| 2201159 | 8/1988 | United Kingdom. | |

OTHER PUBLICATIONS

Chemical Abstracts, vol. 109, No. 212827u, Japanese Application.
Chemical Abstracts, vol. 110, No. 137460j, Japanese Application.
"Oleflex: $C_2$-$C_5$ Dehydrogenation Updated", Vora, Pujado, and Anderson, Energy Progress, (vol. 6, No. 3), pp. 171-176, Sep. 1986.
"The Dehydrogenation of Ethane over Chromium Catalysts", Lugo and Lunsford, Journal of Catalysis, 91, pp. 155-166 (1985).

Primary Examiner—Asok Pal
Attorney, Agent, or Firm—William W. Haefliger

[57] ABSTRACT

An apparatus and system for the dehydrogenation of ethane to produce ethylene and hydrogen through the use of a catalytic ceramic membrane having selective permeability, thus permitting separation of hydrogen from the reaction zone which causes further dehydrogenation of ethane, the catalytic ceramic membrane being in a cylindrical form which has been treated to have a metallic catalyst of suitable metal, such as platinum, palladium or chromium, deposited on the surface adjacent to the reaction zone. The catalytic ceramic membrane tube is enclosed within an alloy tube of suitable composition to permit heating to the temperature range of 300° to 650° C. The annulus surrounding the ceramic membrane tube may be filled with a pelleted catalyst, thus causing the dehydrogenation reaction to take place within this annular zone, but which will be accelerated by the permeation of hydrogen out of the zone through the ceramic catalytic membrane. The reactor is connected to a recovery system which permits separation of pure ethylene and unconverted ethane. A steady stream of $H_2O$ or argon continuously sweeps away the $H_2$ coming out through the selective membrane, thereby further facilitating the conversion process.

7 Claims, 5 Drawing Sheets

PROCESS FOR PRODUCTION OF ETHYLENE FROM ETHANE

BACKGROUND OF THE INVENTION

This invention relates generally to production of ethylene, and more particularly, to high yield process and apparatus for conversion of ethane to ethylene.

Ethylene is one of the most important building block petrochemicals produced in the United States and the world. It is usually produced by thermally cracking hydrocarbon feedstocks ranging from ethane to heavy gas oils. There are other production techniques under investigation for producing ethylene using catalytic systems, auto-catalytic with chlorine and oxygen, and various combinations of such processes.

The most economically viable process currently in industrial use is the pyrolysis of ethane, or ethane/propane mixtures, or light hydrocarbon liquids in the boiling range of 100°–150° F. This process is usually carried out in a high temperature pyrolysis furnace where steam and hydrocarbons are preheated to 300° to 400° C., and then passed through a cracking coil made from very high alloy CrNi steel, where the combined stream is heated to 700°–900° C. The typical yield obtained from such a process treating ethane is as shown in Table 1. The overall conversion of ethane is limited to 55–60 weight percent due to equilibrium and coking considerations and temperature limitations of the metal reactor tube. The unconverted ethane is typically recovered and recycled to permit an overall ultimate conversion of ethane to ethylene in the range of 70–82 weight percent. The by-products produced, as shown in Table 1 below, are hydrogen, methane, propylene, and heavier compounds, all of which require separation from the ethylene product which is usually required to be 99+% pure for use in a commercial process.

TABLE 1

| COMPARISON OF PRODUCT YIELDS IN ETHANE CRACKING PILOT VERSUS INDUSTRIAL UNIT | | |
| --- | --- | --- |
| wt % | Pilot Plant | Industrial |
| $H_2$ | 3.71 | 3.71 |
| $CO/CO_2$ | | 0.26 |
| $CH_4$ | 2.99 | 3.35 |
| $C_2H_2$ | | 0.20 |
| $C_2H_4$ | 48.7 | 48.68 |
| $C_2H_6$ | 39.0 | 39.27 |
| $C_3H_6$ | 1.05 | 1.07 |
| $C_3H_8$ | | 0.21 |
| $C_4H_6$ | 0.99 | 1.12 |
| $C_4H_8$ | | 0.21 |
| $C_4H_{10}$ | | 0.3 |
| $C_5$ | 1.85 | 1.6 |
| Pressure atm. abs. | 1.55 | 1.9 |
| Steam dilution kg/kg | 0.4 | 0.4 |
| Outlet temp C. | 840. | 835. |
| Conversion % | 59.1 | 59.87 |

There is need for an improved process providing significantly higher, or enhanced, ethylene yields.

SUMMARY OF THE INVENTION

It is a major object of the invention to provide method and apparatus meeting the above need. In particular, it is a major object to provide a significantly improved process characterized by ethane to ethylene conversion levels equivalent to two to five times thermodynamic equilibrium for ethylene in an ethane-ethylene exit gas stream, at relatively moderate temperatures.

It has been discovered that a particular process and apparatus employing a catalytic ceramic membrane reactor can be utilized to carry out the dehydrogenation of ethane to produce enhanced ethylene yields (and hydrogen) in a very unique and economic manner. To our knowledge, no prior catalytic processes have proven to be industrially sufficiently practical because of equilibrium limitations, temperature requirements and potential fouling (including coking) problems. An equilibrium diagram for the reaction $$C_2H_6 \rightleftharpoons C_2H_4 + H_2 \tag{1}$$

at atmospheric pressure is shown in FIG. 1. It can be seen that very high temperatures, above 800° C., are required to raise the equilibrium conversion of ethylene above 70%. At these temperatures, there is considerable production of unwanted by-products and coke because of thermal cracking reactions.

According to the process of the present invention, the steps of dehydrogenating ethane to produce ethylene, include:

a) providing a generally tubular, highly porous, asymmetric, ceramic membrane, and providing a heated zone in a container into which the membrane is received, b) the membrane having been treated with a catalytically active metallic substance so as to create an intramembrane catalytic profile, c) and passing a stream of ethane carrying hydrogen in the range of 0.1 to 10% by volume into contact with the treated membrane, at a selected moderate temperature, and in such manner as to cause hydrogen diffusion through the membrane faster than ethane and ethylene, d) whereby the dehydrogenation reaction, ethane to ethylene, proceeds relatively rapidly, to produce hydrogen that passes through the membrane.

As will be seen, the process proceeds at moderately elevated temperatures, between 400° and 600° C. The ceramic membrane is characterized by relative permeabilities for $H_2$, $C_2H_6$ and $C_2H_4$, which are about 3.5, 0.9, and 1.0, respectively, and the process includes the steps of removing $H_2$ at one side of the membrane, and removing $C_2H_6$ and $C_2H_4$ at the other side of the membrane. Also, catalytic pellets containing palladium, platinum or chromium may be employed in the zone from which $H_2$ proceeds through the membrane (i.e., from which $H_2$ proceeds through the membrane) to enhance the catalytic conversion of $C_2H_4$ to $C_2H_6$, and such catalyst is also carried by the porous membrane, as will appear.

Apparatus to effect the conversion typically includes:

a) a generally tubular, highly porous, ceramic membrane, and container for the membrane and forming a heated zone into which it is received, the membrane having been treated with a catalytically active metallic substance so as to create an intramembrane catalytic profile, b) and means for passing a stream of ethane carrying hydrogen in the range of 0.1 to 10% by volume into contact with the treated membrane, at elevated temperature, and in such manner as to cause hydrogen diffusion through the membrane faster than ethane and ethylene, c) whereby the dehydrogenation reaction, ethane to ethylene, proceeds relatively rapidly, to produce hydrogen that passes through the membrane.

These and other objects and advantages of the invention, as well as the details of an illustrative embodiment, will be more fully understood from the following specification and drawings, in which:

DRAWING DESCRIPTION

DETAILED DESCRIPTION

Figure 1:
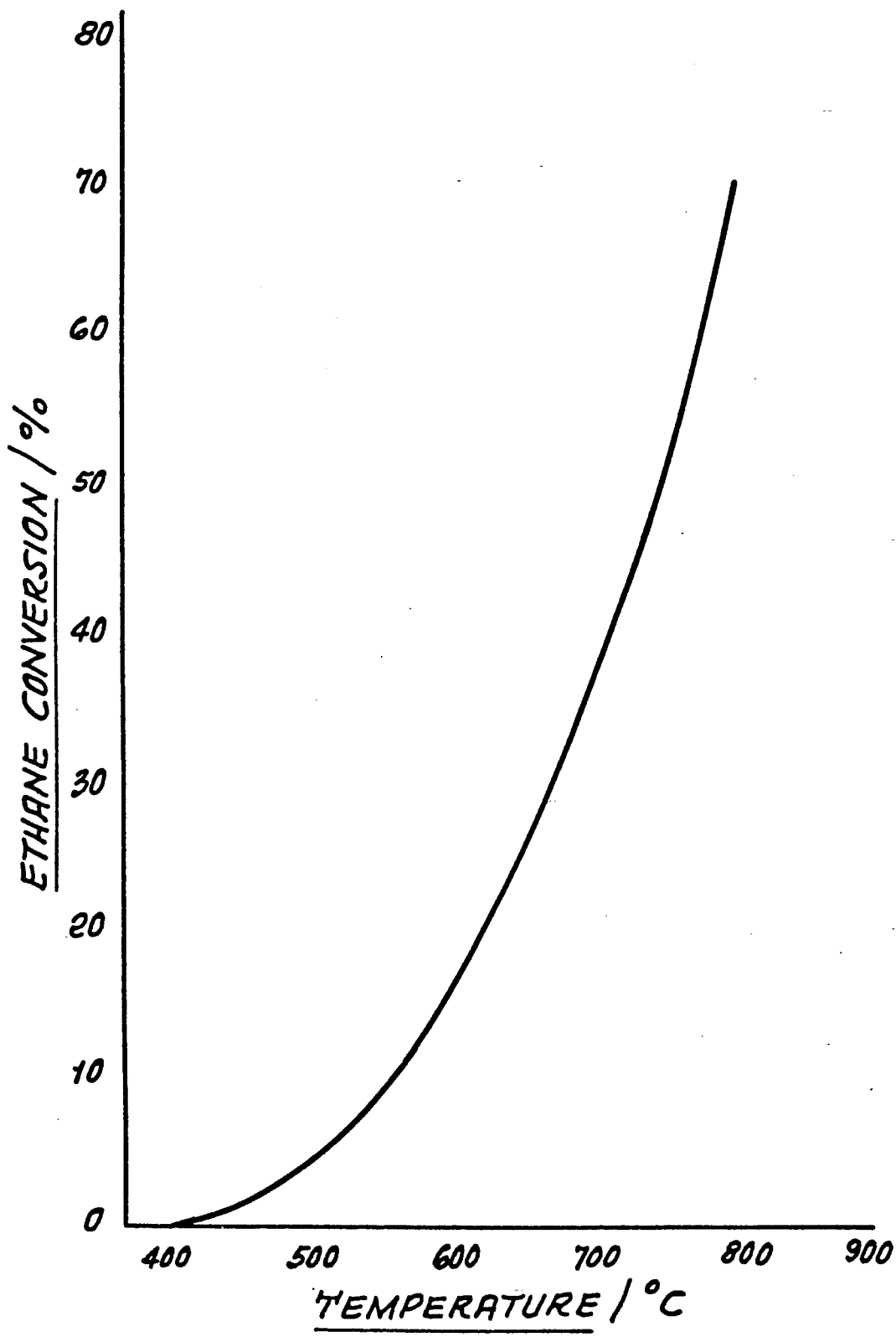
FIG. 1 is a graph showing equilibrium conversion of ethane to ethylene vs. temperature.
Figure 2:
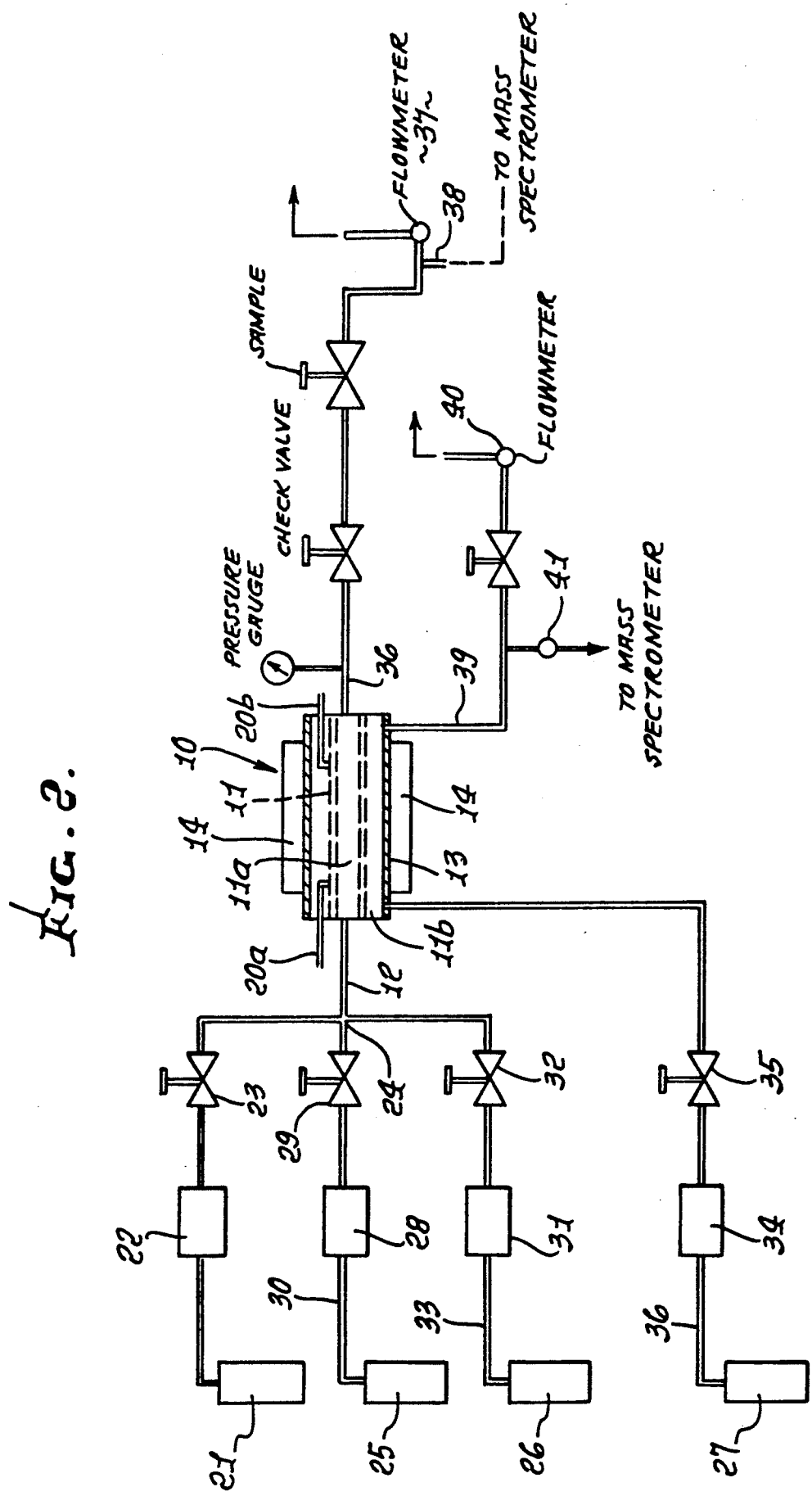
FIG. 2 is a flow diagram.
Figure 4:
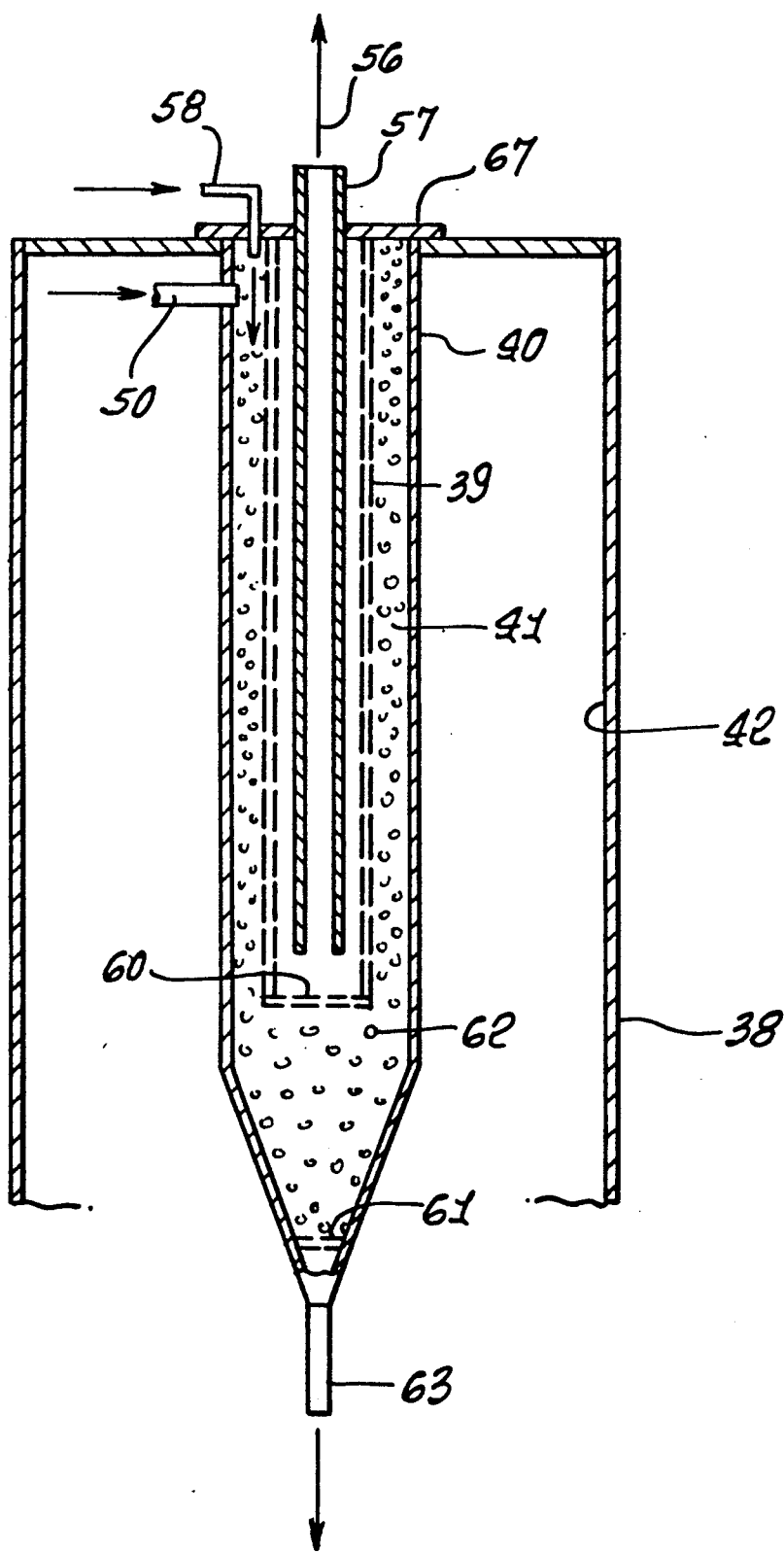
FIG. 4 is a section taken through the reactor apparatus.

In the process of the present invention, a reactor 10, as seen in FIGS. 2 and 4, employs a tubular, highly porous asymmetric ceramic membrane 11 treated with a catalytically-active substance, such as platinum, or other suitable metal, such as palladium or chromium, so as to create an optimal intramembrane catalytic profile. A stream 12 of ethane, carrying hydrogen in the range of 0.1%–10% by volume and steam, if desired, is passed adjacent to the ceramic membrane reactor which typically takes the form of a tube into the interior 11a of which the stream 12 is passed. The membrane reactor is shown as enclosed in a heated metal tube 13, the whole assembly being maintained at 400°–600° C., as by an electrical heater 14, or other means. The hydrogen produced by the dehydrogenation of ethane diffuses transversely through the reactor membrane wall faster than ethane and ethylene, causing the dehydrogenation reaction ethane-to-ethylene to proceed rapidly to give high conversion and yields far beyond the normal thermodynamic equilibrium, at process temperature and pressure. Pressure of the entering stream within interior space 11a is typically between 20 and 30 psi, and the pressure at the outer side of the membrane is kept at atmospheric pressure, i.e., at or near 14.7 psi.

Depletion of hydrogen from the immediate reaction zone favors additional production of hydrogen, and consequently enhanced production of ethylene, i.e., beyond that produced in conventional reactor configurations, since removal of hydrogen from the reaction zone requires more hydrogen to be produced to satisfy the equilibrium according to the equilibrium constant equation:

$$K_p = \frac{(C_2H_4) \cdot (H_2)}{(C_2H_6)} \quad (2)$$

Conversion levels equivalent to two to five times normal thermodynamic equilibrium for ethylene in the combined exit gas at temperatures of 500° to 600° C. have been obtained. Typical results are shown in Table 2 when using apparatus as shown in FIG. 2.

TABLE 2

ETHANE CONVERSION IN A CERAMIC MEMBRANE REACTOR VS. EQUILIBRIUM CONVERSION
ΔP = 10 PSIG, NO SWEEP GAS

| Temperature °C. | ETHANE CONVERSION | |
|---|---|---|
| | Ceramic Membrane Reactor | Equilibrium Conversion |
| 400 | 6.2 | 1.0 |
| 450 | 8.8 | 1.8 |
| 476 | 10.0 | 2.5 |
| 500 | 12.8 | 2.9 |
| 550 | 33.2 | 10.0 |
| 550 | 33.9 | 10.0 |
| 600 | 40.6 | 24.8 |

*Hydrocarbon:Hydrogen:Inert Feed Input Mole Ratios in the range of 1:1:5 to 1:1:10.

With the use of longer residence times, increased catalyst surface and somewhat higher temperatures, 90% to 95% conversion of ethane to ethylene is obtainable without the production of significant quantities of unwanted by-products, and without significant build up of coke, or other foulants, on the catalyst.

Usable ceramic membranes are typically tubular and asymmetric, consisting of a macroporous support layer on which one or several microporous catalyst layers are deposited. One typical membrane consists of gamma-alumina membrane on alpha-alumina support material. The required relative permeabilities for $H_2/C_2H_6/C_2H_4$ are in the range of, or about, 3.5/0.9/1.0 with at least a 90% Knudsen flow component. The catalytic metal is impregnated in the membrane according to a predetermined profile which depends upon (i) the membrane structure, (ii) the intrinsic catalytic activity, (iii) temperature and pressure and flow conditions, and (iv) the specific metallic catalyst, and is deposited on the surface facing the reaction zone, indicated at 19. The rapid diffusion of product hydrogen through the ceramic membrane causes the further dehydrogenation of ethane to occur so that the reaction will move to satisfy the equilibrium relationship by producing more hydrogen (and consequently more ethylene). $H_2$ is removed from the zone at one side of the membrane, and $C_2H_4$ and $C_2H_6$ are removed from the zone at the opposite side of the membrane.

As shown in FIG. 2, the membrane reactor 11 is encased in a heating system 14, including a metal container 13. The tubular reactor has catalyst impregnated on its inner surface. The temperature of the ceramic tube 11, is measured by ("cement-on") thermocouples 20a and 20b. Flow to the reactor consists of ethane flowing from tank 21 through flow controller 22 and valve 23 into the reactor. At the inlet point 24, the ethane stream is mixed with a sweep gas from tank 25 consisting of argon and in addition, a small stream of hydrogen from tank 26 to amount to approximately 0.1% to 10% of the flow of ethane entering the membrane reactor. Tank 27 comprises an additional source of argon which is used to sweep the annulus 11b surrounding the membrane reactor. A differential pressure of 10 to 50 psi is maintained between the inside of the ceramic membrane reactor and the annulus. Note flow controller 28 and valve 29 in series with line 30; flow controller 31 and valve 32 in series with line 33; and flow controller 34 and valve 35 in series with line 36.

As the streams flow through the membrane reactor, the ethane is converted to ethylene and hydrogen at the catalytic surface inside the edge of the membrane reactor tube. Hydrogen diffuses through the membrane wall at a rate approximately 3½ to 4 times the diffusing flow rate of ethylene or ethane. This causes the reaction zone to be depleted of hydrogen and the thermodynamic equilibrium reaction equation causes additional ethane to be dehydrogenated to produce hydrogen to balance the reaction coefficient. The stream 36 leaving the membrane reactor then flows out of the reactor through a bubbling flow meter indicated at 37. A sample is taken from the sample port 38, to flow to a mass spectrometer. Similarly, the stream 39 passing through the annulus flows through a bubbling flow meter indicated at 40. A sample is also taken at the sample port 41, to flow to a mass spectrometer.

Figure 3:
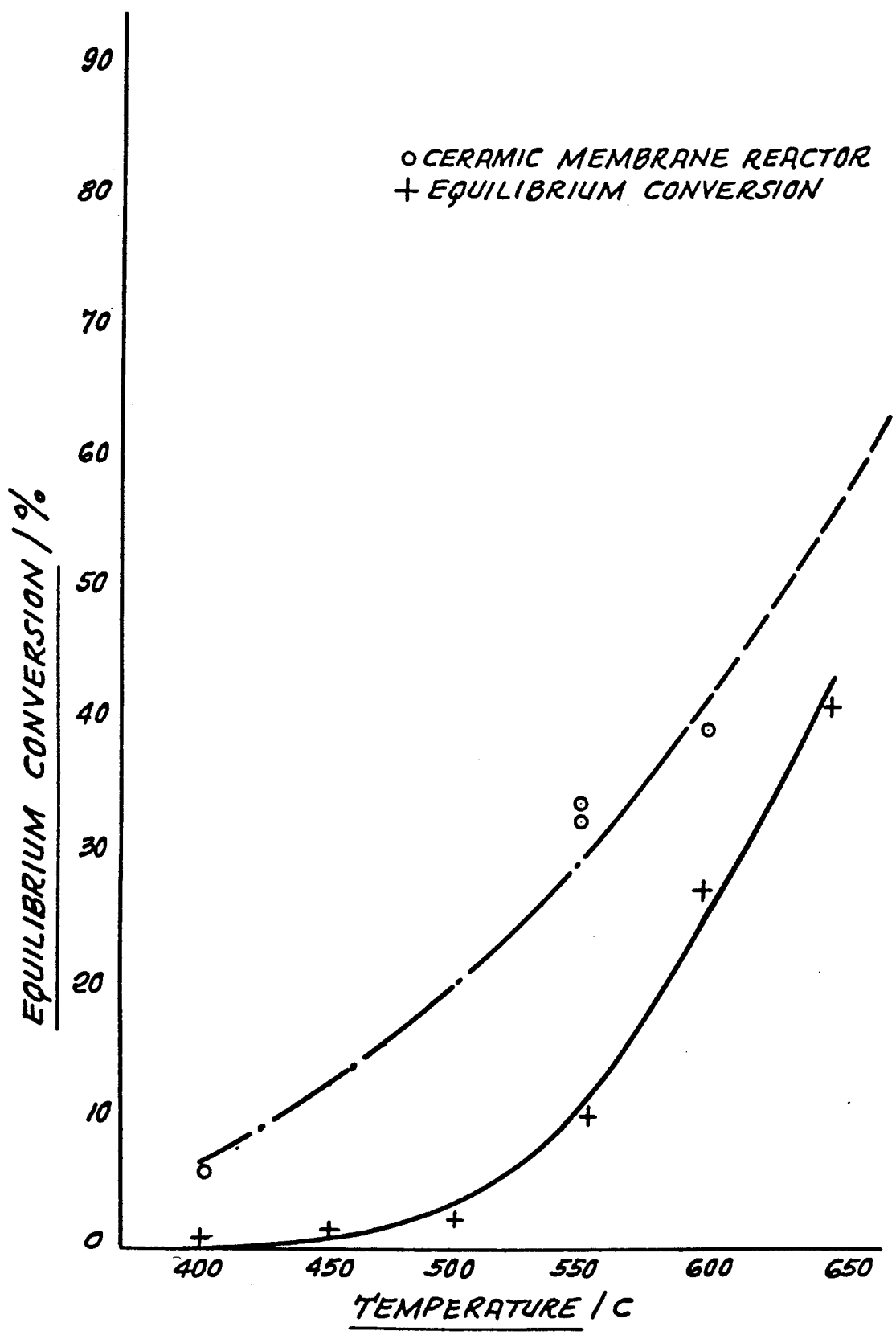
FIG. 3 is a graph showing increased yield of ethylene when using a porous ceramic reactor.

The results obtained are summarized in Table 2 and in FIG. 3, both of which show the conversion levels attained at temperatures in the range of 450° to 650° C. Note that the ethane conversion level achieved in the combined gas streams leaving the reactor ranges from approximately six times to two times the anticipated equilibrium values at the reaction zone temperatures for thermodynamic considerations and the equilibrium equation. The described apparatus was used to obtain the data given herein. Projections of yields for the different temperatures of industrial operations show that use of appropriate catalyst areas and reactor volumes result in the conversion of ethane in a single pass or multiple pass system of the order of 90% to 95% to ethylene. Such conversion levels are attainable with a minimum production of by-products other than hydrogen. This enables a high degree of economic advantage to the present system, for production of ethylene.

An embodiment of the design for a commercial scale system is shown in FIG. 4. The ceramic membrane 39 is located within an alloy tube 40. The entire system is enclosed within a flame-heated furnace 38 capable of driving the temperature within the reactor to the desired level of 400° to 650° C. The level of temperature is selected to cause the rate of reaction to reach a reasonable level, and thus permit economic limits on the size of the reactor necessary for reasonable conversion levels and reasonable throughputs.

In a typical design, the external tube 40 is a 4-inch to 6-foot diameter stainless steel enclosure, whereas the membrane reactor 39, located within the tube, is approximately 1 inch to 4 feet in diameter. The overall length of the ceramic membrane tube is of the order of 3 feet to 10 feet. The ceramic membrane tube is of a composition as described below, as in Table 5.

TABLE 5

| | Material | Pore Diameter | Thickness |
| --- | --- | --- | --- |
| Layer 1 | gamma alumina | 40 angstroms | 5 microns |
| Layer 2 | alpha alumina | 0.2 microns | 30 microns |
| Layer 3 | alpha alumina | 0.8 microns | 50 microns |
| Support | alpha alumina | 10 to 15 microns | 1.5 to 2.0 millimeters |

Metallic catalytic material is impregnated on the external surface of the ceramic membrane tube and consists of a suitable impregnation of platinum, palladium, or other metal, to give a concentration of the order of 5% to 10% by weight of the surface material. The method for the preparation of the catalytic impregnation is as follows: The ceramic membrane tube is wet impregnated with chloroplatinic acid solution (Alfa products, Johnson Matthey) diluted to 5-15 weight percent. The tube is dried overnight and subsequently placed into the reactor body. A 60% argon, 40% oxygen mixture is passed through the reactor over the catalyst at 130° C. overnight. Finally, hydrogen is passed over the catalyst at 350° C. for 12 hours.

Referring again to the FIG. 4, the inlet gas consists of ethane plus 0.1% to 10% hydrogen by volume, entering through port 50, then passing down through the reaction tube enclosure 39 in an annular vessel or container 40 surrounding the ceramic membrane. The space 41 between the container 40 and the membrane 39 may be filled with pelleted catalyst 62 (palladium, alumina or silica pellets impregnated with platinum, or ($r_2O_3$)) to provide a sufficient catalytic residence time for the conversion of ethane to ethylene. Hydrogen formed in the reaction zone diffuses rapidly through the ceramic membrane into the central zone 55 within the tube, and is continuously withdrawn at 56 via exit tube 57. Additional hydrogen, if required for balancing purposes, is introduced through connection 58 into the ceramic tube central zone 41. The bottom of the ceramic membrane tube is closed by a plate 60 which can be either porous or nonporous, depending upon the mode of operation desired. A second bottom plate 61 provides permeable support for the pelleted catalyst 62 (if used) filling the annulus between the ceramic membrane tube and the reactor enclosure tube. The annulus product gases, which are depleted in hydrogen and contain most of the ethylene product, leave through the reactor outlet 63. Hydrogen and some ethylene, together with some ethane, leave through the central outlet tube 56. The entire assembly is heated by the radiant wall 42 of the furnace. The ceramic material of the tube 39 consists for example of a gamma alumina membrane on an alpha-alumina support.

Figure 5:
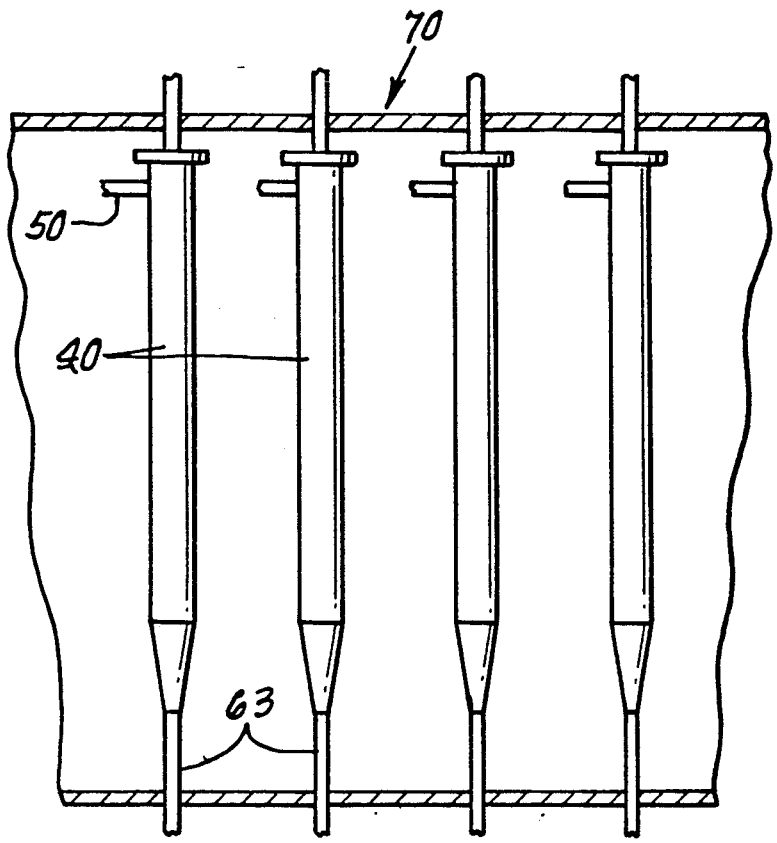
FIG. 5 shows use of multiple reactors, in accordance with the invention.

The described apparatus meets several important design requirements. The ceramic tube is supported by a plate 67 at the top of the reactor and is mounted in a vertical position, permitting free thermal expansion and contraction, and thus freedom from mechanical stress brought about by differential expansion between the ceramic tube in the center and the metallic alloy tube 40 enclosing the catalyst and the ceramic tube. In practice, a battery of such parallel, vertical tubes 40 is mounted within an overall furnace enclosure 70 permitting an economic design of the type illustrated in FIG. 5. As an example, a furnace containing a battery of twenty vertical tubes 40 permits the production of 10,000 tons per year of ethylene from ethane at a conversion level of better than 95%, and with the production of only hydrogen gas as a by-product, with a minimum amount of higher hydrocarbon materials to separate.

Figure 6:
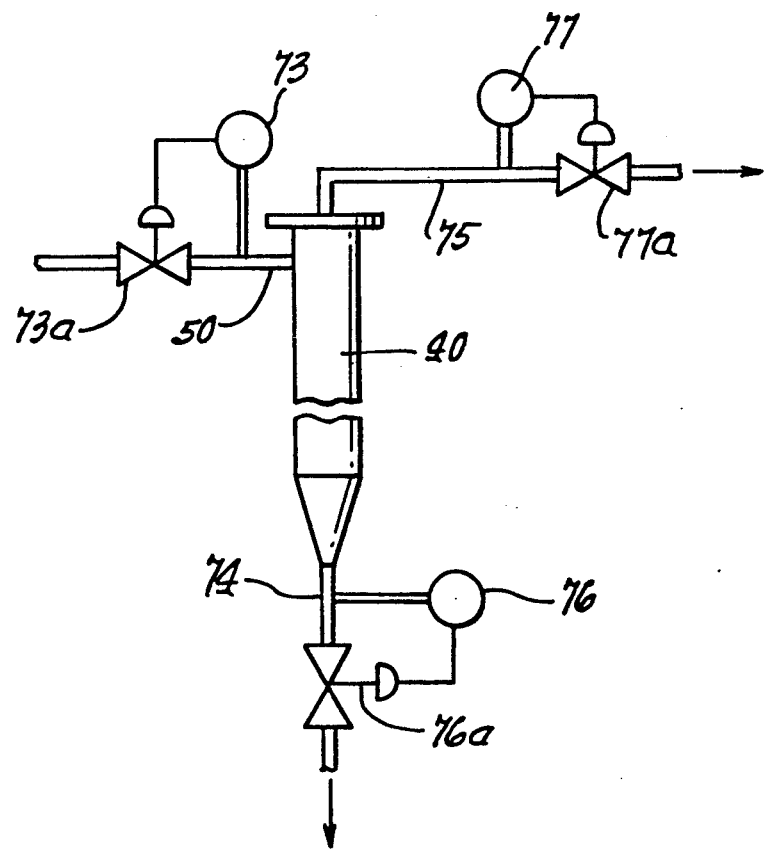
FIG. 6 is like FIG. 4, but also showing flow controls.

In carrying out the reaction, differential pressure is maintained between the entering stream of ethane and hydrogen and the exit stream, or permeate, leaving the inside of the catalytic membrane of the ceramic membrane material, by use of appropriate control instrumentation. This is illustrated in FIG. 6, wherein the flow of the inlet feed stream at 50 is controlled by a flow recorder controller 73, resetting a differential pressure device 73a, and the exiting flows at 74 and 75 are maintained at differential pressures with respect to the inlet flow by means of additional pressure-controlling devices 76 and 76a, and 77 and 77a. Differential pressure across the membrane is maintained at between 10 and 50 psi.

This type of reactor leads to a typical overall material balance as shown in Table 3 as follows.

TABLE 3

MATERIAL BALANCE FOR
CATALYTIC CERAMIC MEMBRANE REACTOR

| | Feed mol/hr | Product mol/hr | Permeate mol/h |
|---|---|---|---|
| Ethane | 100 | 5 | 5 |
| Ethylene | — | 85 | 5 |
| Hydrogen | 5 | 10 | 85 |
| | 105 | 100 | 95 |

The 100 moles per hour of ethane entering the system is converted into 90 moles per hour of ethylene. Of the 90 moles per hour of ethylene, 85 moles per hour appear in the product gas along with 5 moles per hour of unconverted ethane and typically, 10 moles per hour of hydrogen. The exit gas, which is rich in hydrogen, contains 85 moles per hour of hydrogen and 5 moles per hour of ethylene plus 5 moles per hour of ethane. This type of composition can be readily handled in a simple separation system utilizing an expander-compressor tandem followed by an appropriately designed distillation column. The type of separation system employed is less complicated than that used in a conventional thermal cracking plant, because the product gas contains so few components and essentially zero unwanted heavy by-product materials. Hydrogen produced in the system is available for export to other uses and for recycle to the reactor to maintain the appropriate hydrogen balance. The presence of hydrogen in the reactor feed system is very important to maintain the catalyst at a high level of activity, and suppresses the formation of carbon and coke on the surface of the catalyst (which would otherwise shorten its normal operating life).

As an alternate to the expander/compressor system, a molecular sieve or other adsorbent separation system can be used for the recovery of pure ethylene. The above design considerations enable a comparison of economics for the production of ethylene from ethane using a) the herein described catalytic ceramic membrane process, as against, b) conventional thermal cracking processes.

A typical ceramic reactor has cylindrical membrane wall thickness of about 5 microns on a 1.5-2 millimeter thick support layer.

We claim:

1. The process for dehydrogenating ethane to produce ethylene, that includes
   a) providing a generally tubular, highly porous, asymmetric, ceramic membrane, and providing a heated reaction zone in a container into which the membrane is received,
   b) said membrane having been impregnated with a catalytically active metallic substance so as to create an intramembrane catalytic profile, with pore diameters less than 100 Å,
   c) and passing an inlet stream of ethane carrying hydrogen in the range of 0.1% to 20% by volume into contact with the treated membrane, at one side thereof at elevated temperature between 300° and 800° C. and in such manner as to cause hydrogen diffusion through the membrane to the opposite side thereof faster than ethane and ethylene, and removing an outlet stream of hydrogen from said opposite side of the membrane, and removing an outlet stream of ethylene from said one side of the membrane,
   d) whereby the dehydrogenation reaction, ethane to ethylene, proceeds relatively rapidly, with the result that the conversion of ethane to ethylene exceeds the normal thermodynamic equilibrium value for the temperature and pressure of the reactor without removal of hydrogen from the reaction zone,
   e) the membrane characterized as having relative permeabilities for $H_2$, $C_2H_6$ and $C_2H_4$ of at least 3.5, 0.9, and 10, respectively, and that are within 90% of Knudsen flow component diffusivities,
   f) controlling the flow of said inlet and outlet streams to maintain a differential pressure between said inlet ethane stream, and said outlet hydrogen stream of between 10 and 100 psi,
   g) and maintaining said container at said elevated temperature and radiating heat from said container toward said reaction zone to maintain said elevated temperature,
   h) and providing a pelleted catalyst material adjacent to the side of the membrane to which said stream of ethane is passed,
   i) said container being metallic and substantially tubular, and including the initial step of removing an ethylene-containing gas stream from the container,
   j) and employing argon or steam to sweep $H_2$ away from said opposite side of the membrane, and employing argon or steam to mix with $C_2H_6$ fed to said one side of the membrane.

2. The process of claim 1 including the initial step of removing an ethylene-containing gas stream from the container.

3. The process of claim 1 including providing multiple individual ceramic membrane reactors in spaced relation, each constructed and operating as in claim 1, to thereby form a vertical tubular system of reactors to permit unrestricted thermal and mechanical expansion/contraction of the individual ceramic membrane reactors.

4. The process of claim 3 including arranging individual of said reactors in a furnace in a battery of two or more reactors.

5. The process of claim 3 wherein the product ethylene is separated from ethane and hydrogen in said system of reactors followed by an adsorption separation system or low temperature distillation to produce an ethylene product which is at least 85% pure.

6. The process for dehydrogenating a mixture of ethane and propane to produce a mixture of ethylene and propylene that includes
   a) providing a generally tubular, highly porous, asymmetric, ceramic membrane, and providing a heated reaction zone in a container into which the membrane is received,
   b) said membrane having been impregnated with a catalytically active metallic substance so as to create an intramembrane catalytic profile, with pore diameters less than 100 Å,
   c) and passing an inlet stream of ethane and propane, carrying hydrogen in the range of 1.0% to 20% by volume, into contact with the treated membrane, at one side thereof at elevated temperature between 300° and 800° C. and in such manner as to cause hydrogen diffusion through the membrane to the opposite side thereof faster than ethane, ethylene, propane, and propylene, and removing an outlet stream of hydrogen from said opposite side of the membrane, and removing an outlet stream of ethylene and propylene from said one side of the membrane,
d) whereby the dehydrogenation reactions, ethane to ethylene, and propane to propylene proceed relatively rapidly, to produce hydrogen that passes through the membrane, with the result that the conversions of ethane to ethylene and propane to propylene exceed the normal thermodynamic equilibrium values for the temperature and pressure of the reactor without removal of hydrogen with the reaction zone,
e) the membrane characterized as having relative permeabilities for $H_2$, ethane, ethylene, propane, and propylene that are within 90% of Knudsen flow component diffusivities,
f) controlling the flow of said inlet and outlet streams to maintain a differential pressure between said inlet ethane and propane stream, and said outlet hydrogen stream, of between 10 and 100 psi,
g) maintaining said container at said elevated temperature and radiating heat from said container toward said reaction zone to maintain said elevated temperature,
h) providing a pelleted catalyst material adjacent to the side of the membrane to which said inlet stream of ethane and propane is passed,
i) said container being metallic and substantially tubular, and including the initial step of removing an ethylene-containing gas stream from the container,
j) and employing argon or steam to sweep $H_2$ away from said opposite side of the membrane, and employing argon or steam to mix with ethane and propane fed to said one side of the membrane.

7. The process of dehydrogenating an alkane or a mixture of alkanes to produce alkene or a mixture of alkenes, that includes
a) providing a generally tubular, highly porous, asymmetric, ceramic membrane, and providing a heated reaction zone in a container into which the membrane is received,
b) said membrane having been impregnated with a catalytically active metallic substance so as to create an intramembrane catalytic profile, with pore diameters less than 100 Å,
c) and passing an inlet stream of said alkane or mixture of alkanes, carrying hydrogen in the range of 0.1% to 20% by volume, into contact with the treated membrane, at one side thereof at elevated temperature between 300° and 800° C., and in such manner as to cause hydrogen diffusion through the membrane to the opposite side thereof faster than alkane, alkene, or said mixture of alkanes or alkenes, and removing an outlet stream of hydrogen from said opposite side of the membrane, and removing an outlet stream of alkene or a mixture of alkenes from said one side of the membrane,
d) whereby the dehydrogenation reactions, alkane to alkene, or said mixture of alkanes to said mixture of alkenes, proceeds relatively rapidly, to produce hydrogen that passes through the membrane, with the result that the conversions of alkane to alkene, or mixture of alkanes to mixture of alkenes, exceed the normal thermodynamic equilibrium value for the temperature and pressure of the reactor without removal of hydrogen from the reaction zone,
e) the membrane characterized as having relative permeabilities for $H_2$, alkane, alkene, mixture of alkanes and mixture of alkenes that are within 90% of Knudsen flow component diffusivities,
f) controlling the flow of said inlet and outlet streams to maintain a differential pressure between said inlet stream of alkane or mixture of alkanes, and said outlet hydrogen stream, of between 10 and 100 psi,
g) maintaining said container at said elevated temperature and radiating heat from said container toward said reaction zone to maintain said elevated temperature,
h) providing a pelleted catalyst material adjacent to the side of the membrane to which said inlet stream of said alkane or mixture of alkenes is passed,
i) said container being metallic and substantially tubular, and including the initial step of removing an ethylene-containing gas stream from the container,
j) and employing argon or steam to sweep $H_2$ away from said opposite side of the membrane, and employing argon or steam to mix with alkane fed to said one side of the membrane.

* * * * *